US008592568B2

(12) United States Patent
Shah et al.

(10) Patent No.: US 8,592,568 B2
(45) Date of Patent: Nov. 26, 2013

(54) NUCLEIC ACID PROBES AND METHODS FOR DETECTING PLASMODIUM PARASITES

(75) Inventors: Jyotsna S. Shah, Santa Clara, CA (US); Danuta Wronska, Raleigh, NC (US); Helena Weltman, Los Altos, CA (US); Nick S. Harris, Monterey, CA (US); Suzanne Scherini-Ward, Santa Clara, CA (US); Oliva Mark, San Jose, CA (US)

(73) Assignee: ID-Fish Technology, Santa Clara, CA (US)

( * ) Notice: Subject to any disclaimer, the term of this patent is extended or adjusted under 35 U.S.C. 154(b) by 0 days.

(21) Appl. No.: 13/085,799

(22) Filed: Apr. 13, 2011

(65) Prior Publication Data

US 2011/0287422 A1 Nov. 24, 2011

Related U.S. Application Data

(63) Continuation of application No. 11/998,251, filed on Nov. 29, 2007, now Pat. No. 7,927,801.

(51) Int. Cl.
*C07H 21/04* (2006.01)
*C12Q 1/68* (2006.01)

(52) U.S. Cl.
USPC ...................... 536/24.32; 435/6.15

(58) Field of Classification Search
None
See application file for complete search history.

(56) References Cited

U.S. PATENT DOCUMENTS

| 5,519,127 A | 5/1996 | Shah et al. |
| 5,629,156 A | 5/1997 | Shah et al. |
| 5,792,609 A | 8/1998 | Wataya et al. |
| 6,165,723 A | 12/2000 | Shah et al. |
| 2007/0042358 A1 | 2/2007 | Shah |

FOREIGN PATENT DOCUMENTS

| JP | 2003250564 A | 9/2003 |
| WO | WO 98/35057 A1 | 8/1998 |

OTHER PUBLICATIONS

Chai, J-Y. et al. Am. J. Trop. Med. Hyg. 63(1,2):80-84 (2000).*
Das, A. et al. Molecular and Cellular Probes 9:161 (1995).*
Waters, A.P. and McCutchan, T.F. Nucleic Acids Research 17(5):2135 (1989).*
Qari, S.H. et al. Gene 150:43 (1994).*
McCutchan, T.F. et al. Molecular and Biochemical Parasitology 28:63 (1988).*
Lal, A.A. et al. Molecular and Biochemical Parasitology 36:67 (1989).*
Waters, A.P. and McCutchan, T.F. The Lancet 333(8651):1343 (1989).*
Machouart et al., Development of a PCR assay follwed by nonradioactive hybridization using oligonucleotides covalently bound to CovaLink NH microwells for Detection of four Plasmodium species in blood samples from humans. Journal of Clinical Microbiology. Sep. 2006, vol. 44, No. 9, pp. 3279-3284, see entire reference particularly pp. 3281-3282.
Ausubel, et al., Current Protocols in Molecular Biology, Greene Publishing, New York, N.Y., 1994.
Database Biosis [Online] Biosciences Information Service, Philadelphia, PA, US; Jan. 2001, Perandin F et al: "Usefulness of genus-specific PCR and Southern blot species-specific hybridization for the detection of imported malaria cases in Italy". Database accession No. PREV200100129987; & Microbiologica (PAVIA), vol. 24, No. 1, Jan. 2001, pp. 69-76, ISSN: 1121-7138.
Database Biosis [Online] Biosciences Information Service, Philadelphia, PA, US; Apr. 2004, Calderaro A et al: "Evaluation of a new plate hybridization assay for the laboratory diagnosis of imported malaria in Italy" Database accession No. PREV200400315161; & New Microbiologica, vol. 27, No. 2, Apr. 2004, pp. 163-171, ISSN: 1121-7138.
Ayyanathan K et al: "Development of specific DNA probes and their usage in the detection of Plasmodium vivax infection in blood." Molecular and Cellular Probes Aug. 1995 LNKD-PUBMED: 7477019, vol. 9, No. 4, Aug. 1995, pp. 239-246, XP002587734, ISSN: 0890-8508.
Holmberg M et al.: "A comparison of two DNA probes, one specific for Plasmodium falciparum and one with wider reactivity, in the diagnosis of malaria" Transactions of the Royal Society of Tropical Medicine and Hygiene, Elsevier GB LNKD-DOI:10.1016/0035-9203(90)90255-D, vol. 84, No. 2, Mar. 1, 1990, pp. 202-205, XP02310713ISSN: 0035-9203 [retrieved on Mar. 1, 1990].
Database EMBL [Online] Mar. 19, 2003, "E271 early-oocyst library Plasmodium berghei/Anopheles stephensi mixed EST library cDNA clone E271, mRNA sequence." retrieved from EBI accession No. EMBL:CB367357 Database accession No. CB367357.
Database EMBL [Online] Mar. 19, 2003, E104 early-oocyst library Plasmodium berghei/Anopheles stephensi mixed EST library cDNA clone E104 similar to Plasmodium berghei small subunit rRNA, mRNA sequence. retrieved from EBI accession No. EMBL:CB367404. Database accession No. CB367404.
Database EMBL [Online] Mar. 2, 2006 (2006:03-7.02)T"Plasmodium-berghei-strANKA-cDNA-clone:-OKO10339; ookinete 5' Est." retrieved from EBI accession No. EMBL:BB980173 Database accession No. BB980173.
Database EMBL [Online] Mar. 3, 2004, "1393 Plasmodium yoelii liver stage LCM cDNA library Plasmodium yoelii cDNA, mRNA sequence." retrieved from EBI accession No. EMBL:CK573353 Database accession No. CK573353.

(Continued)

*Primary Examiner* — Diana Johannsen
(74) *Attorney, Agent, or Firm* — Pierce Atwood LLP; Kevin M. Farrell; David J. Wilson

(57) ABSTRACT

This invention relates to novel nucleic acid probes and methods for detecting *Plasmodium* parasites as well as detecting different *Plasmodium* parasites selectively from one another.

6 Claims, No Drawings

(56) References Cited

OTHER PUBLICATIONS

Database EMBL [Online] Jan. 25, 1995, "SSUrRNA {malaria patient blood sample 9007] [Plasmodium vivax, Yunnan isolate, Genomic, 641 nt]." retrieved from EBI accession No. EMBL:S69871 Database accession No. S69871; & Database Medline [Online] US National Library of Medicine (NLM), Bethesda, MD, US; 1993, Wan L et al: "[Amplification, cloning and sequence analysis of a SSUrRNA gene fragment of Plasmodium vivax isolates from Yunnan Province]". Database accession No. NLM8174219.

Database EMBL [Online]February 20, 1989, "P.falciparum 18S ribosomal RNA in asexual parasites." retrieved from EBI accession No. EMBL:M19172 Database accession No. M19172; & McCutchan T F et al: "Primary sequences of two small subunit ribosomal RNA genes from Plasmodium falciparum" Molecular and Biochemical Parasitology, Elsevier Science Publishers, Amsterdam, NL LNKD-DOI:10.1016/0166-6851(88)90181-8, vol. 28, No. 1, Feb. 1, 1988, pp. 63-68.

Database EMBL [Online] Jan. 11, 2001, "Plasmodium falciparum 3D7 cDNA clone from Sugano malaria cDNA library: XPFn2712." retrieved from EBI accession No. EMBL:AU086528 Database accession No. AU086528; & Watanabe J et al: "Full-malaria: a database for a full-length enriched cDNA library from human malaria parasite, Plasmodium falciparum. "Nubleic Acids Research Jan. 1, 2001 LNKD-PUBMED: 11125052, vol. 29, No. 1, Jan. 1, 2001, pp. 70-71, ISSN: 1362-4962.

De Monbrison F et al: "Simultaneous identification of the four human Plasmodium species and quantification of Plasmodium DNA load in human blood by real-time polymerase chain reaction" Transactions of the Royal Seciety of Tropical Medicine and Hygiene, Elsevier, GB LNKD-DOI:10.1016/S0035-9203(03)90065-4, vol. 97, No. 4, Jul. 1, 2003, pp. 387-390, XP004545531ISSN: 0035-9203.

Rougemont M et al: "Detection of four Plasmodim species in blood from humans by 18S rRNA gene subunit-based and species-specific real-time PCR assays" Journal of Clinical Microbiology, Amterican Society for Microbiology, Washington, DC, US LNKD-DOI:10. 1128/jcm.42.12.5636-5643.2004, vol. 42, No. 12, Dec. 1, 2004, pp. 5636-5643, XP00249283ISSN: 0095-1137.

Machouart, "Development of a PCR Assay Followed by Nonradioactive Hybridization Using Oligonucleotide4s Covalently Bound to CovaLink NH Microwells for Detection of Four Plasmodium Species in Blood Samples from Humans" Journal of Clinical Microbiology, vol. 44, No. 9, Sep. 2006, pp. 3279-3284.

* cited by examiner

NUCLEIC ACID PROBES AND METHODS FOR DETECTING PLASMODIUM PARASITES

BACKGROUND OF THE INVENTION

*Plasmodium* is a genus of parasitic protozoa. Infection with this genus is known as malaria. The parasite always has two hosts in its life cycle: a mosquito vector and a vertebrate host. At least ten species infect humans including *P. falciparum, P. vivax, P. malariae,* and *P. ovale*. Malaria is an infectious disease that is widespread in tropical and subtropical regions. Malaria represents a threat to survival of men, women and children. It infects between 300 and 500 million people every year and causes between one and three million deaths annually, mostly among young children in Sub-Saharan Africa.

Malaria is one of the most common infectious diseases and an enormous public-health problem. The disease is caused by protozoan parasites of the genus *Plasmodium*. The most serious forms of the disease are caused by *Plasmodium falciparum* and *Plasmodium vivax*, but other related species (*Plasmodium ovale* and *Plasmodium malariae*) can also infect humans. Determining the infectious species helps determine the course of treatment for the patient.

The preferred and most reliable diagnosis of malaria is microscopic examination of blood films because each of the four major parasite species has distinguishing characteristics. Two sorts of blood film are traditionally used. Thin films are similar to usual blood films and allow species identification because the parasite's appearance is best preserved in this preparation. Thick films allow the microscopist to screen a larger volume of blood and are about eleven times more sensitive than the thin film, so picking up low levels of infection is easier on the thick film, but the appearance of the parasite is much more distorted and therefore distinguishing between the different species can be much more difficult.

From the thick film, an experienced microscopist can detect parasite levels (or parasitemia) down to as low as 0.0000001% of red blood cells. However, microscopic diagnosis can be difficult because the early trophozoites ("ring form") of all four species look identical and it is never possible to diagnose species on the basis of a single ring form; species identification is always based on several trophozoites.

In areas where microscopy is not available, there are antigen detection tests that require only a drop of blood. OptiMAL-IT® (TCS Bio Sciences, Buckingham, England) will reliably detect falciparum down to 0.01% parasitemia and non-falciparum down to 0.1%. Paracheck-Pf® (Orchard Biomedical Systems, India) will detect parasitemias down to 0.002% but will not distinguish between falciparum and non falciparum malaria. Parasite nucleic acids may also be detected using polymerase chain reaction. This technique is more accurate than microscopy. However, it is expensive and requires a specialized laboratory. Moreover, levels of parasitemia are not necessarily correlative with the progression of disease, particularly when the parasite is able to adhere to blood vessel walls. Limited molecular methods are available in some clinical laboratories and rapid real-time assays, for example, QT-NASBA (real-time quantitative nucleic acid sequence-based amplification) based on the polymerase chain reaction) but are only now being developed. Therefore, sensitive, low-tech diagnosis tools need to be developed for in order to detect low levels of parasitaemia in the field.

What is need are reagents and methods for the rapid and accurate detection and discrimination of various malaria causing *Plasmodium* species.

SUMMARY OF THE INVENTION

This invention relates to nucleic acid probes that detect and discriminate between different species of *Plasmodium* parasites in, for example, hybridization assays. Accordingly, in a first aspect, the invention features nucleic acid fragments to be used as probes for detecting *Plasmodium* in a hybridization assay. The invention also includes probes (DNA, RNA and PNA) that can discriminate between *P. falciparum, P. vivax, P. malariae* and *P. ovale*. In the context of the present invention the term "discriminates between" (or similar terms) means that the probe binds to nucleic acid (e.g., RNA, DNA, rRNA [ribosomal RNA] or rDNA [ribosomal DNA]) from one species more favorably than the other 3 species.

In a second aspect, the invention features a nucleic acid fragment containing a sequence selected from, preferably, at least five, more preferably at least ten or most preferably at least fifteen consecutive nucleotides or the entire sequence of one or more of probes designated PGenus1, PGenus2, Mal F1, MalF2, Mal1.8F, Mal1.8R, PV1, PV2, PF1, PF2, PF3, PF4, PF5, PM1, PO1 or the partial or full-length complementary sequences thereof.

In a third aspect, the invention features a nucleic acid fragment containing a sequence selected from at least five, preferably, at least ten, more preferably at least thirteen or most preferably at least fifteen consecutive nucleotides or the entire sequence of one or more of probes designated SEQ ID NO: 1 through SEQ ID NO.: 15 or the partial or full-length complementary sequences thereof.

In a final aspect, the invention features a method for detecting the presence of *Plasmodium* in a sample. In this method, a sample is contacted with a nucleic acid fragment containing a sequence selected from, preferably, at least five, at least ten, more preferably at least thirteen or most preferably at least fifteen consecutive nucleotides or the entire sequence of a PGenus1, PGenus2, Mal F1, MalF2, Mal1.8F, Mal1.8R, PV1, PV2, PF1, PF2, PF3, PF4, PF5, PM1 or PO1, probe selected from or the partial or full-length complementary sequence thereof (or any combination thereof); under conditions that permit the nucleic acid fragment to hybridize to *Plasmodium* nucleic acid. Detection of the nucleic acid fragment bound to the *Plasmodium* nucleic acid in the sample is used as an indication of the presence of *Plasmodium* in the sample. Detection with probes of the present invention that discriminate between the four species of *Plasmodium* listed above indicates the presence of that species of *Plasmodium*.

In one embodiment of this aspect of the invention, the nucleic acid fragment contains a sequence selected, preferably, from at least five, more preferably at least ten or most preferably at least fifteen consecutive nucleotides or the entire sequence of probe PGenus1 or the full-length complementary sequence thereof.

In a second embodiment of this aspect of the invention, the nucleic acid fragment contains a sequence selected, preferably, from at least five, more preferably at least ten or most preferably at least fifteen consecutive nucleotides or the entire sequence of probe PGenus2, or the full-length complementary sequence thereof.

In a third embodiment of this aspect of the invention, the nucleic acid fragment contains a sequence selected from, preferably, at least five, more preferably at least ten or most preferably at least fifteen or the entire sequence of probe MalF1 or the full-length complementary sequence there of.

In yet another embodiment of this aspect of the invention, the nucleic acid fragment contains a sequence selected from, preferably, at least five, more preferably at least ten or most preferably at least fifteen nucleotides, or the entire sequence of probe MalF2 or the full-length complementary sequence thereof.

In yet another embodiment of this aspect of the invention, the nucleic acid fragment contains a sequence selected from, preferably, at least five, more preferably at least ten or most preferably at least fifteen nucleotides or the entire sequence of probe Mal1.8F or the full-length complementary sequence thereof.

In yet another embodiment of this aspect of the invention, the nucleic acid fragment contains a sequence selected from, preferably, at least five, more preferably at least ten or most preferably at least fifteen nucleotides or the entire sequence of probe Mal1.8R, or the full-length complementary sequence thereof.

An advantage of probes PGenus 1, PGenus2, MalF1, MA1F2, Mal1.8F and Mal1.8R is that while they detect all three species of *Plasmodium* tested and, thus, are not limited to detecting a single *Plasmodium* species. Other features and advantages of the present invention will be apparent from the following detailed description thereof and also from the appended claims.

In specific aspects, the present invention contemplates a method for detecting the presence of *Plasmodium* in a sample, said method comprising the steps of: contacting said sample with a probe for detecting *Plasmodium* in a hybridization assay, wherein said probe discriminates between *Plasmodium* species, under conditions that permit said probe to hybridize to *Plasmodium* nucleic acid; and detecting said probe bound to said *Plasmodium* nucleic acid in said sample as an indication of the presence of *Plasmodium* in said sample.

In the preceding embodiment, the nucleic acid fragment comprises a sequence that is selected from at least five consecutive nucleotides of probe PV1, PV2, PF1 PF3, PF4, PF5, PM1 or PO1 the full-length complementary sequence thereof.

In other aspects, the present invention contemplates a method for detecting the presence of *Plasmodium* in a sample, said method comprising the steps of: contacting said sample with a nucleic acid fragment comprising a sequence selected from at least five consecutive nucleotides of a probe selected from a group consisting of PGenus1, PGenus2, MalF1, MalF2, Mal1.8F, Mal1.8R, PV1, PV2, PF1, PF2, PF3, PF4, PF5, PM1 and PO1 or full-length complementary sequence thereof, under conditions that permit said nucleic acid fragment to hybridize to *Plasmodium* nucleic acid; and detecting said nucleic acid fragment bound to said *Plasmodium* nucleic acid in said sample as an indication of the presence of *Plasmodium* in said sample.

In the preceding embodiment, the nucleic acid fragment comprises of a sequence selected from the full length sequence, at least fifteen consecutive nucleotides, at least ten consecutive nucleotides, at least five consecutive nucleotides of a probe selected from a group consisting of PGenus1, PGenus2, MalF1, MalF2, Mal1.8F, Mal1.8R, PV1, PV2, PF1, PF2, PF3, PF4, PF5, PM1 and PO1 or full-length complimentary sequence thereof.

The present invention also contemplates a nucleic acid fragment comprising a sequence selected from at least five consecutive nucleotides of a probe selected from a group consisting of PGenus1, PGenus2, MalF1 and MalF2, Mal1.8F, Mal1.8R, PV1, PV2, PF1, PF2, PF3, PF4, PF5, PM1, PO1 or the full-length complementary sequence thereof.

The present invention also contemplates a nucleic acid fragment comprising a sequence selected from at least ten consecutive nucleotides of a probe selected from a group consisting of PGenus1, PGenus2, MalF1 and MalF2, Mal1.8F, Mal1.8R, PV1, PV2, PF1, PF2, PF3, PF4, PF5, PM1, PO1 or the full-length complementary sequence thereof.

The present invention also contemplates a nucleic acid fragment comprising the complete sequence selected of a probe selected from a group consisting of PGenus1, PGenus2, MalF1 and MalF2, Mal1.8F, Mal1.8R, PV1, PV2, PF1, PF2, PF3, PF4, PF5, PM1, PO1 or the full-length complementary sequence thereof.

In specific aspects, the present invention contemplates a method of selecting nucleic acid probes that discriminate between the species *P. falciparum, P. vivax, P. malariae* and *P. ovale*, the method comprising: preparing a nucleic acid fragment or polypeptide nucleic acid, PNA corresponding to, or complementary to, a sequence of at least five nucleotides of nucleic acid from *P. falciparum, P. vivax, P. malariae* and *P. ovale*; comparing the ability of the probe to detect one or more of the *Plasmodium* species in a hybridization assay; and selecting the probe or probes that detect one, two or three species of *Plasmodium* but not all four species of *Plasmodium*.

The present invention also contemplates a method for detecting and differentiating between *P. falciparum, P. Vivax, P. malariae* and *P. ovale* in a sample, said method comprising: providing: i) a sample from a subject suspected of having malaria and ii) probes comprising nucleic acid suitable for detecting and differentiating between *P. falciparum, P. Vivax, P. malariae* and *P. ovale*; contacting said sample with said probes under conditions suitable for hybridization of said probes to targets; and determining the presence of *P. falciparum, P. Vivax, P. malariae* and *P. ovale*, if any, in the sample.

In one embodiment, the method contemplates that the probe for detecting *P. falciparum* is selected from a nucleic acid sequence of at least five contiguous nucleotides of one or more of PF1, PF2, PF3, PF4 or PF5. In another embodiment, the method contemplates that the probe is selected from a nucleic acid sequence of at least ten contiguous nucleotides of one or more of PF1, PF2, PF3, PF4 or PF5. In yet another embodiment, the method contemplates that the probe is selected from a nucleic acid sequence of at least fifteen contiguous nucleotides of one or more of PF1, PF2, PF3, PF4 or PF5.

In one embodiment, the method contemplates that the probe for detecting *P. Vivax* is selected from a nucleic acid sequence of at least five contiguous nucleotides of one or more of PV1 or PV2. In another embodiment, the method contemplates that the probe is selected from a nucleic acid sequence of at least ten contiguous nucleotides of one or more of PV1 or PV2. In yet another embodiment, the method contemplates that the probe is selected from a nucleic acid sequence of at least fifteen contiguous nucleotides of one or more of PV1 or PV2.

In one embodiment, the method contemplates that the probes for detecting *P. malariae* are selected from a nucleic acid sequence of at least five contiguous nucleotides of PM1 and one or more of PF1, PF2, PF3, PF4 or PF5 and wherein a sample is positive for *P. malariae* if the probe of at least five contiguous nucleotides of PM1 tests positive and the probe of at least five contiguous nucleotides of PF1, PF2, PF3, PF4 or PF5 tests negative. In another embodiment, the method contemplates that the probes are selected from a nucleic acid sequence of at least ten contiguous nucleotides of one or more of PF1, PF2, PF3, PF4 or PF5 and at least ten contiguous nucleotides of PM1. In yet another embodiment, the method contemplates that the probes are selected from a nucleic acid sequence of at least fifteen contiguous nucleotides of one or more of PF1, PF2, PF3, PF4 or PF5 and at least fifteen contiguous nucleotides of PM1.

In one embodiment, the method contemplates that the probes for detecting P. ovale are selected from a nucleic acid sequence of at least five contiguous nucleotides of PO1 and one or more of PF1, PF2, PF3, PF4 or PF5 and wherein a sample is positive for P. ovale if the probe of at least five contiguous nucleotides of PO1 tests positive and the probe of at least five contiguous nucleotides of PF1, PF2, PF3, PF4 or PF5 tests negative. In another embodiment, the method contemplates that the probes are selected from a nucleic acid sequence of at least ten contiguous nucleotides of one or more of PF1, PF2, PF3, PF4 or PF5 and at least ten contiguous nucleotides of PO1. In yet another embodiment, the method contemplates that the probes are selected from a nucleic acid sequence of at least fifteen contiguous nucleotides of one or more of PF1, PF2, PF3, PF4 or PF5 and at least fifteen contiguous nucleotides of PO1.

In any of the preceding embodiments, the probe or probes used may be of the entire nucleotide sequence as disclosed herein or the complementary strand thereof as well as the complementary sequence of the five, ten or fifteen contiguous nucleotides of the probes.

DETAILED DESCRIPTION OF THE INVENTION

The invention features nucleic acid probes for detecting Plasmodium parasites (e.g., P. falciaprum, P. vivax, P. malariae and P. ovale) in, for example, hybridization assays. The probes of the invention may be used in methods for detecting the presence of Plasmodium in a biological sample. In these methods, a probe of the invention is contacted with a biological sample (e.g., whole blood, CSF or a tissue sample) in a hybridization assay and detection of the probe bound to the nucleic acid in the sample is used as an indication of the presence of Plasmodium in the sample. Probes included in the invention may be identified by:

A (1) preparing a nucleic acid fragment or polypeptide nucleic acid, PNA (i.e., a probe) corresponding to, or complementary to, a sequence of at least ten nucleotides of nucleic acid from P. falciparum and (2) comparing the ability of the probe to detect all the Plasmodium species in a hybridization assay. Probes that hybridize to P. falciparum more favorably than to other three species are included in the invention.

B (1) preparing a nucleic acid fragment or PNA (i.e., a probe) corresponding to, or complementary to, a sequence of at least ten nucleotides of nucleic acid from P. vivax and (2) comparing the ability of the probe to detect all the Plasmodium species in a hybridization assay. Probes that hybridize to P. vivax more favorably than to other three species are included in the invention.

C (1) preparing a nucleic acid fragment or PNA (i.e., a probe) corresponding to, or complementary to, a sequence of at least ten nucleotides of nucleic acid from P. malaiiae and (2) comparing the ability of the probe to detect all the Plasmodium species in a hybridization assay. Probes that hybridize to P. malariae more favorably than to other three species are included in the invention.

D (1) preparing a nucleic acid fragment or PNA (i.e., a probe) corresponding to, or complementary to, a sequence of at least ten nucleotides of nucleic acid from P. ovale and (2) comparing the ability of the probe to detect all the Plasmodium species in a hybridization assay. Probes that hybridize to P. ovale more favorably than to other three species are included in the invention.

P. falciaprum, P. vivax, P. malariae and P. ovale nucleic acid may be obtained from biological samples (such as whole blood, bone marrow, CSF) from infected individuals, using standard nucleic acid isolation methods in the art. P. falciaprum (as well as P. vivax, P. malariae and P. ovale) can also be obtained from culture. For example, DNA encoding Plasmodium ribosomal RNA may be obtained by PCR amplification of DNA prepared from a whole blood sample of an infected patient using the methods and primers described herein and known in the art.

Any Plasmodium sequence (e.g., a sequence encoding 5S, 5.8S, 18S, or 28S ribosomal RNA) may be selected as a candidate sequence for the identification of probes. Preferred sequences are those that diverge from analogous sequences in non-human Plasmodium or other protozoan parasites like, for example, Babesia or Thileria, as determined by phylogenetic comparison. The nucleic acid probes of the invention are at least 10 nucleotides in length and may contain deoxyribonucleotides (DNA probes), ribonucleotides (RNA probes), peptide nucleic acid (PNA probes) or combinations or modifications thereof. The probes may be single stranded or double stranded and may be prepared by any of a number of standard methods in the art. For example, the probes may be made by chemical synthesis, restriction endonuclease digestion of a vector (e.g., a plasmid containing a sequence corresponding to the probe), polymerase chain reaction (PCR) amplification, or in vitro transcription of a vector containing a sequence corresponding to the probe (see, e.g., Ausubel, et al., Current Protocols in Molecular Biology, Greene Publishing, New York, N.Y., 1994, incorporated herein by reference). The probes may be labeled during or after synthesis. For example, labeled nucleotides containing, e.g., radioisotopes (e.g., p32, S35, or H3), biotin or digoxigenin may be incorporated into the probe during synthesis. Probes containing biotin are detected by the use of a secondary reagent such as avidin or streptavidin, which contains a detectable label such as a fluorochrome (e.g., fluorescein or rhodamine) or an enzyme (e.g., alkaline phosphatase or horseradish peroxidase). Similarly, probes containing digoxigenin may be detected by using a labeled antidigoxigenin antibody. Probes may also be labeled after synthesis by, e.g., nick translation or the use of T4 RNA ligase, poly(A) polymerase, terminal transferase or T4 polynucleotide kinase, in standard methods (see, e.g., Ausubel, et al., supra). The probes may also contain modified nucleotides in order to increase the stability of the probe. For example, ribonucleotides containing 2'-0-alkyl groups on the ribose group may be used. The probes may also contain modifications that facilitate capture of the probe onto a solid support. For example, poly-dA or poly-deaza-guanosine tails may be added to the 3' ends of the probes, using terminal transferase, in order to facilitate probe binding to a solid support, e.g., poly-dT or poly-dC labeled magnetic particles. The probes may be purified prior to use, using standard methods such as denaturing polyacrylamide gel electrophoresis, high performance liquid chromatography or gel filtration chromatography (see, e.g., Ausubel, et al., supra). The probes of the invention may be used in any standard hybridization assay to detect the presence of Plasmodium in a sample. For example, Southern blot, dot blot, in situ hybridization, real-time hybridization detection by biosensors or dual probe, sandwich-type hybridization assays may be used (see, e.g., U.S. patent application Ser. No. 07/826,657 [now U.S. Pat. No. 5,519,127] and U.S. Pat. No. 5,629,156 [International Publication Number WO 94/10335], all of which are incorporated herein by reference). Alternatively, the probes may be used as primers in a polymerase chain reaction assay (see, e.g., Ausubel, et al., supra). Biological samples that may be analyzed using the probes and methods of the invention include whole blood, CSF, bone marrow and tissue samples from, e.g., the spleen. Nucleic acid is extracted from the sample by standard methods (except in the case of in situ hybridization, where the cells are kept intact) and is analyzed using the probes in the assays listed above. A single probe or combinations of probes may be used in the assay. The hybridization conditions used with the probes (e.g., in the methods of the invention) fall within the range of, for example, 30-50% formamide at 25° C.-42° C. or mixtures of GuSCN and formamide between 25-37° C. As is "known by one skilled in the art," selection of hybridization conditions depends on the length and nucleotide content (i.e., GC compared to AT) of the probe. Accordingly, hybridization conditions may be adjusted to accommodate these factors. In addition, the use of different salts (e.g., guanidine thiocyanate or guanidine hydrochloride compared with NaCl) and denaturing agents (e.g., NP-40, sodium dodecyl sulfate) may require adjustment of the salt concentration and the temperature, as can readily be determined by one skilled in the art.

Non-limiting examples of hybridization conditions that may be used in the present invention are as follows. In Southern blot analysis, the following hybridization conditions may be used: 30% to 50% formamide in 2×SSC at 42° C. After hybridization, the filters are washed using standard methods. For example, three 15 minute post-hybridization washes at 25° C. in 2×SSC to 0.1×SSC and 0.1% SDS may be carried out in order to remove unbound probes. For RNA blots hybridizations in 30% formamide at room temperature overnight were performed. Excess probes were removed by washing three 15 min washes in 2×SSC with 0.1% SDS.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G-C ratio within the nucleic acids. A single molecule that contains pairing of complementary nucleic acids within its structure is said to be "self-hybridized."

It is well known that numerous equivalent conditions may be employed to comprise suitable hybridization conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

For in situ hybridization, the following conditions may be used as described in U.S. Pat. No. 6,165,723 and US Patent Publication No. 2007/0042358 (which are herein incorporated by reference): GuSCN (1.5 to 3.5 M depending on the probe sequence) between room temperature and 37° C. or mixtures of GuSCN and formamide between room temperature and 37° C. for 30 minutes to one hour, followed by washes in SSC (2× to 0.1×) and 0.1% SDS.

Exemplification

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever.

Hybridization of probes PGenus1, PGenus2, Ma1F1, Ma1F2, Mal1.8F, Mal1.8R to *P. falciaprum, P. vivax, P. ovale* and *P. malariae* Samples.

Dot-blot analysis data is shown in Table 1. In these experiments, approximately 0.1 ug of a plasmid containing nucleotide sequences encoding the respective 18S rRNA subunits was used per spot. The blots were hybridized with dig-labeled probes under the hybridization conditions described above.

In case of RNA, RNA was synthesized and 0.1 ug in 6×SSC was spotted on nitrocellulose membrane. Hybridization with the dig-labeled probes (digoxigenin-labeled probes) was performed overnight at room temperature in formamide. This method was used to compare hybridization signals between the different organisms and probes.

Probes which hybridize to all species of 18 rDNA of all species of *Plasmodium* are PGenus1, PGenus2, MalF1, MalF2, Mal1.8F and Mal1.8R. Probes PGenus1, PGenus2 and Mal1.8R hybridized to 18S rRNA of all the *Plasmodium* species.

*Plasmodium* Genus 18S rRNA-Specific Probes

*Plasmodium* genus specific probes of the invention include probes PGenus1, PGenus2, MalF1, MalF2, Mal1.8F and Mal1.8R which have the sequences:

```
PGenus1
                                        (SEQ ID NO: 1)
5'-TCTCGCTTGCGCGAATACTCG-3'

PGenus2
                                        (SEQ ID NO: 2)
5'-CCAAAGACTTTGATTTCTCAT-3'

Malf1
                                        (SEQ ID NO: 3)
5'-CAGATACCGTCGTAATCTTA -3'

Malf2
                                        (SEQ ID NO: 4)
5'-CGAAAGTTAAGGGAGTGAAGAC-3'

Mal1.8F
                                        (SEQ ID NO: 5)
5'-atgtagaaactgcgaacggc -3'

Mal1.8R
                                        (SEQ ID NO: 6)
5'-cagcacaatctgatgaatcatgc-3'
```

*Plasmodium* Species 18S rRNA-Specific Probes

*Plasmodium* species specific probes of the invention include probes PV1 which have the sequences of a probe selected from PV1, PV2, PV3, PF1, PF2, PF3, PF4, PF5, PF6 PF7, PF8, PM1, PO1 or the full-length complementary sequence thereof.

```
P. vivax Specific Probes
PV1
                                        (SEQ ID No: 7)
5'-TCTAAGAATAAACTCCGAAGAGAAAATTCTTATTTT-3'

PV2
                                        (SEQ ID No: 8)
5'-TACACACTCAAGAAATGAATCAAGAGTGC-3'
```

*P. falciparum* Specific Probes

PF1
(SEQ ID NO: 9)
5'-GCAATCTAAAAGTCACCTCGAAAGATGACTT-3'

PF2
(SEQ ID No: 10)
5'-CCTAACAAATACTTATCCAAAGATAAAAATCAAGGA-3'

PF3
(SEQ ID No: 11)
5'-ATTTTTAACACTTTCATCCAACACCTAGTCG-3'

PF4
(SEQ ID No: 12)
5'-TTACAAAACCAAAAATTGGCCTTGCATTGTTATTT-3'

PF5
(SEQ ID No: 13)
5'-TCCAATTGTTACTCTGGGAAGG-3'

*P. malariae* Specific Probe

PM1
(SEQ ID No: 14)
5'-GAAACACTCATATATAAGAATGTCTC-3'

*P. ovale* Specific Probe

PO1
(SEQ ID No: 15)
5'-AATTTCCCCGAAAGGAATTTTC-3'

TABLE 1

| Probes | *P. falciparum* | *P. vivax* | *P. malariae* | *P. ovale* |
|---|---|---|---|---|
| PGenus1 | Positive | Positive | Positive | Positive |
| PGenus2 | Positive | Positive | Positive | Positive |
| MalF1 | Positive | Positive | Positive | Positive |
| MalF2 | Positive | Positive | Positive | Positive |
| Mal1.8F | Positive | Positive | Positive | Positive |
| Mal1.8R | Positive | Positive | Positive | Positive |

TABLE 1-continued

| Probes | *P. falciparum* | *P. vivax* | *P. malariae* | *P. ovale* |
|---|---|---|---|---|
| PV1 | Negative | Positive | Negative | Negative |
| PV2 | Negative | Positive | Negative | Negative |
| PF1 | Positive | Negative | Negative | Negative |
| PF2 | Positive | Negative | Negative | Negative |
| PF3 | Positive | Negative | Negative | Negative |
| PF4 | Positive | Negative | Negative | Negative |
| PF5 | Positive | Negative | Negative | Negative |
| PM1 | Positive | Negative | Positive | Negative |
| PO1 | Positive | Negative | Negative | Positive |

Note:
All the probes except MalF1, MalF2 and Mal1.8F hybridize to rRNA also.

In one exemplification of the present invention, samples are tested for the presence of *Plasmodium* sp. and detected *Plasmodium* species are differentiated by use of the probes of the present invention. A sample is tested with probes of at least five, ten or fifteen contiguous nucleotides of probes PV1 and/or PV2, probes PF1, PF2, PF3, PF4 and/or PF5, probes PM1 and probe PO1, or the entire probe or the complementary sequences thereof. Samples that test positive for probes PV1 and/or PV2 are determined to be infected with *P. vivax*. Samples that test positive for probes PF1, PF2, PF3, PF4 and/or PF5 are determined to be infected with *P. falciparium*. Samples that test positive for probes PM1 but not for PF1, PF2, PF3, PF4 and/or PF5 are determined to be infected with *P. malariae*. Samples that test positive for probes PO1 but not for PF1, PF2, PF3, PF4 and/or PF5 are determined to be infected with *P. ovale*.

From the above description, one skilled in the art can easily ascertain the essential characteristics of the present invention and, without departing from the spirit and scope thereof, can make various changes and modifications of the invention to adapt it to various usages and conditions. Thus, other embodiments are also within the claims.

What is claimed is:

1. A composition suitable for detecting *Plasmodium* in a sample, said composition comprising one or more of: a probe consisting of PV1 [SEQ ID NO.: 7] or the full-length complementary sequence thereof, and a label; a probe consisting of PV2 [SEQ ID NO.: 8] or the full-length complementary sequence thereof, and a label; and a probe consisting of PF2 [SEQ ID NO.: 10] or the full-length complementary sequence thereof, and a label.

2. The composition of claim 1, wherein said composition comprises the probe consisting of PV1 [SEQ ID NO.: 7] or the full-length complementary sequence thereof, and a label.

3. The composition of claim 1, wherein said composition comprises the probe consisting of PV2 [SEQ ID NO.: 8] or the full-length complementary sequence thereof, and a label.

4. The composition of claim 1 wherein said composition comprises the probe consisting of PF2 [SEQ ID NO.:10] or the full-length complementary sequence thereof, and a label.

5. The composition of claim 1, wherein the *Plasmodium* to be detected is *Plasmodium vivax* and said composition comprises one or more probes selected from the group consisting of: a probe consisting of PV1 [SEQ ID NO.: 7] or the full-length complementary sequence thereof, and a label; and a probe consisting of PV2 [SEQ ID NO.: 8] or the full-length complementary sequence thereof, and a label.

6. The composition of claim 1, wherein the *Plasmodium* to be detected is *Plasmodium falciparum* and said composition comprises the probe consisting of PF2 [SEQ ID NO.:10] or the full-length complementary sequence thereof, and a label.

\* \* \* \* \*

SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tctcgcttgc gcgaatactc g                                           21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ccaaagactt tgatttctca t                                           21

<210> SEQ ID NO 3
<211> LENGTH: 20
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 3
cagataccgt cgtaatctta                                              20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cgaaagttaa gggagtgaag ac                                           22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
atgtagaaac tgcgaacggc                                              20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cagcacaatc tgatgaatca tgc                                          23

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tctaagaata aactccgaag agaaaattct tatttt                            36

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tacacactca agaaatgaat caagagtgc                                    29

<210> SEQ ID NO 9
<211> LENGTH: 31
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 9
gcaatctaaa agtcacctcg aaagatgact t                                        31

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cctaacaaat acttatccaa agataaaaat caagga                                   36

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
atttttaaca ctttcatcca acacctagtc g                                        31

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ttacaaaacc aaaaattggc cttgcattgt tattt                                    35

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tccaattgtt actctgggaa gg                                                  22

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gaaacactca tatataagaa tgtctc                                              26

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 15
aatttccccg aaaggaattt tc                                           22
```